United States Patent [19]
Morrison

[11] Patent Number: 4,873,982
[45] Date of Patent: Oct. 17, 1989

[54] EXAMINATION GARMENT

[76] Inventor: Judith A. Morrison, 651 Fabyan Rd., Indianapolis, Ind. 46217

[21] Appl. No.: 261,331

[22] Filed: Oct. 24, 1988

[51] Int. Cl.[4] ............................................. A61B 5/00
[52] U.S. Cl. .................................... 128/630; 604/346; 2/DIG. 7
[58] Field of Search ...................... 128/67, 138 R, 630, 128/744, 883; 2/163, 168, DIG. 7; 434/113, 267; 383/3, 118; 604/346

[56] References Cited

U.S. PATENT DOCUMENTS

| | | | |
|---|---|---|---|
| 2,694,396 | 11/1954 | Paschal | 128/67 |
| 3,154,789 | 11/1964 | Lewis | 2/92 |
| 4,135,497 | 1/1979 | Meyers et al. | 128/736 |
| 4,657,021 | 4/1987 | Perry et al. | 128/630 |

OTHER PUBLICATIONS

Newsweek, "Looking for Lumps", Oct. 31, 1988, p. 77.

Primary Examiner—Max Hindenburg
Assistant Examiner—Randy Citrin
Attorney, Agent, or Firm—Woodard, Emhardt, Naughton, Moriarty & McNett

[57] ABSTRACT

A garment useful for examining for lumps under skin, the garment comprising first and second plies, wherein the first ply is form-fitting; and said first and second plies have contacting surfaces which glide easily over each other so that an effective examination can be conducted. Methods for examining for lumps or irregularities in a surface use principles embodied in the above examination garment.

6 Claims, 3 Drawing Sheets

EXAMINATION GARMENT

BACKGROUND OF THE INVENTION

This invention relates generally to methods for examining surfaces for lumps or irregularities, and more particularly to a method and garment useful in self or clinical examinations to detect lumps in the breast area.

It is often necessary to examine for lumps or irregularities in or underneath the skin which may indicate the presence of tumors or other disorders. For example, in recent years, there has been a growing public concern about the rising incidence of breast cancer in women. With about 115,000 new cases of breast cancer being reported each year, it is estimated that one out of every eleven women will develop breast cancer at some time in her life. For a more complete discussion of this disorder, see generally *The American Cancer Society Cancer Book*, Doubleday & Company, Inc., Garden City, N.Y. (1986), Ch. 17.

Because the early detection of breast cancer aids in its effective treatment, much literature has been produced advising that the breast area should be regularly examined for irregularities or lumps, which may reflect the presence of tumors or other disorders. As a part of breast self-examination, it is generally advised that women should begin by examining the surface of their skin using flat fingers to glide over every part of the breasts, feeling for lumps. It is often recommended that this procedure be performed in a bathtub or shower with soap and water so that the skin may be lubricated to reduce friction between the fingers and the skin. See, for example, *The American Cancer Society Cancer Book*, supra, Ch. 17 p. 304. This limitation may unnecessarily inconvenience those wanting to perform self-examination.

Additionally, particularly in office examinations, but also in self-examinations, problems of exposure, modesty and embarrassment arise. U.S. Pat. No. 3,154,789 to Lewis describes a disposable examination garment which is designed to mitigate these problems. The Lewis patent discloses a pancho-style garment formed to drape over the breast area and which may be displaced to allow examination of either breast without exposure of the other. This is accomplished by providing a centrally located vertical slit which divides the front of the garment into two flaps. However, the garment in Lewis does not address the problem of friction between the examiner's hand and the area of the examinee to be examined. Additionally, it is during the physical aspects of examination, i.e. feeling for lumps, that problems of modesty and embarrassment may be particularly acute. Nevertheless, using the garment described in the Lewis patent, the area being examined remains exposed during this part of the examination.

What is therefore needed in these arts is an examination garment which effectively reduces the friction encountered when feeling for lumps or irregularities and allows areas to remain covered during the same. Applicant's invention addresses this need.

SUMMARY OF THE INVENTION

The instant invention generally provides a garment which is useful for examining a surface for lumps or irregularities comprising two contacting plies wherein the inner, contacting surfaces of the plies have a low coefficient of friction between them and thus glide easily over each other. In a preferred embodiment, the garment is especially adapted to fit around the upper torso and over the breast area of an individual, and facilitates examination for lumps or irregularities in the breast area and axillary area which may be indicative of breast cancer. The invention also provides a method for examining for lumps or irregularities in a surface using principles embodied in the above-described examination garment.

DESCRIPTION OF THE PREFERRED EMBODIMENT

Figure 1:
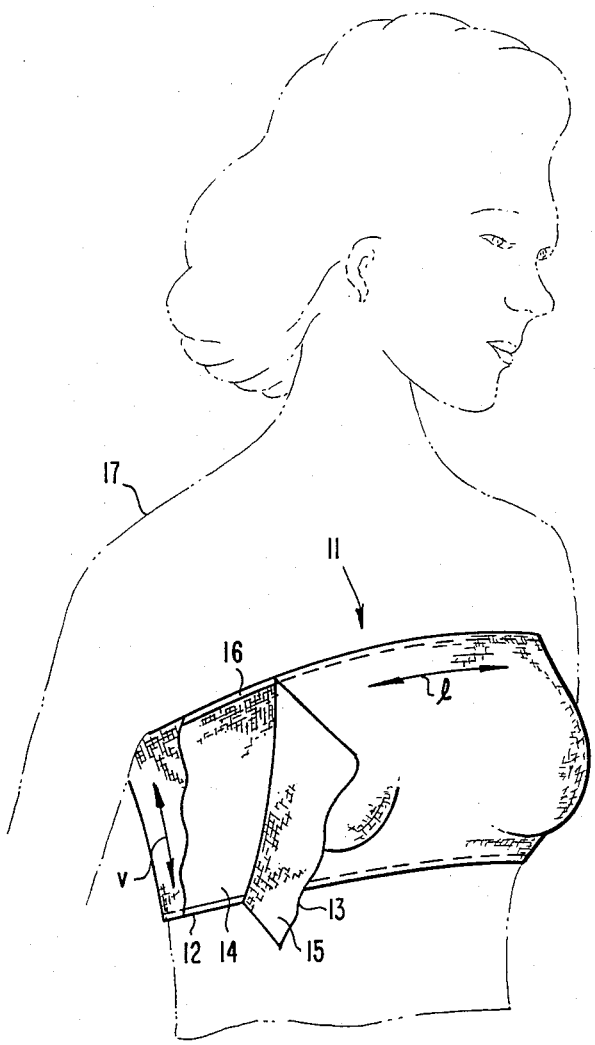
FIG. 1 is a perspective view of a two-ply examination garment having a portion of the outer ply folded back.

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, shown is a perspective view of applicant's preferred examination garment 11 especially adapted to fit around the upper torso and over the breast area of an examinee 17. The garment 11 has an inner ply 12 and an outer ply 13, a portion of which is folded back to reveal various aspects of the garment 11. The contacting faces 14 and 15 of the inner ply 12 and the outer ply 13 are constructed such that there is a low coefficient of friction between them and therefore glide easily over one another. To date, applicant has preferably used material known as SENSUA SOLIDS Style No. 56090 to construct both plies of applicant's preferred examination garment. This material is produced by Guilford Mills of New York, N.Y., and comprises 85% ANTRON nylon and 15% LYCRA brand spandex elastic yarn. One side of this SENSUA SOLIDS material is markedly glossy while the other side is generally more dull. The material is also characterized in that it is relatively elastic in one direction (direction of dominant elasticity), while relatively inelastic in a direction perpendicular thereto.

Applicant has found that two pieces of this SENSUA SOLIDS material, when contacted in the following manner, exhibit a relatively low coefficient of friction and thus glide easily over each other. First, the glossy sides of the pieces must be contacted. Second, the directions of dominant elasticity of the two pieces must be perpendicular to each other. It is believed that when two pieces of the above-noted Sensua Solids material are contacted in this manner, the kinetic coefficient of friction between them is on the order of 0.3 or less. Thus, in applicant's preferred garment, the inner contacting surfaces 14 and 15 of the plies 12 and 13 comprise the shiny side of the above-described SENSUA SOLIDS material. Additionally, the direction of dominant elasticity in the inner ply 12 and the outer ply 13 are perpendicular to each other with the inner ply being dominantly elastic in the direction indicated as "1" in FIG. 1 and the outer ply being dominantly elastic in the direction of "v". In yet another feature of applicant's preferred garment, bands of elastic material 16 are sewn into the upper and lower portions of the garment to help hold it in place on the examinee.

It is believed that surfaces exhibiting kinetic coefficients of friction between about 0.0 to 0.4 would be most effective for the garments of this invention. It is understood, however, that this is only an estimate and that surfaces which glide easily enough over each other to allow an effective examination for lumps are appropriate for the inner contacting surfaces of the plies of the garment 11. Additionally, the applicant recognizes that there are numerous features of a fabric which, taken together, may result in its frictional properties. These features could include, for instance, the nature of the substance used to make the fabric as well as the particular knit of the fabric. Additionally, applicant contemplates that fabrics or their surfaces may be treated with appropriate substances to alter their frictional properties.

Figure 2:
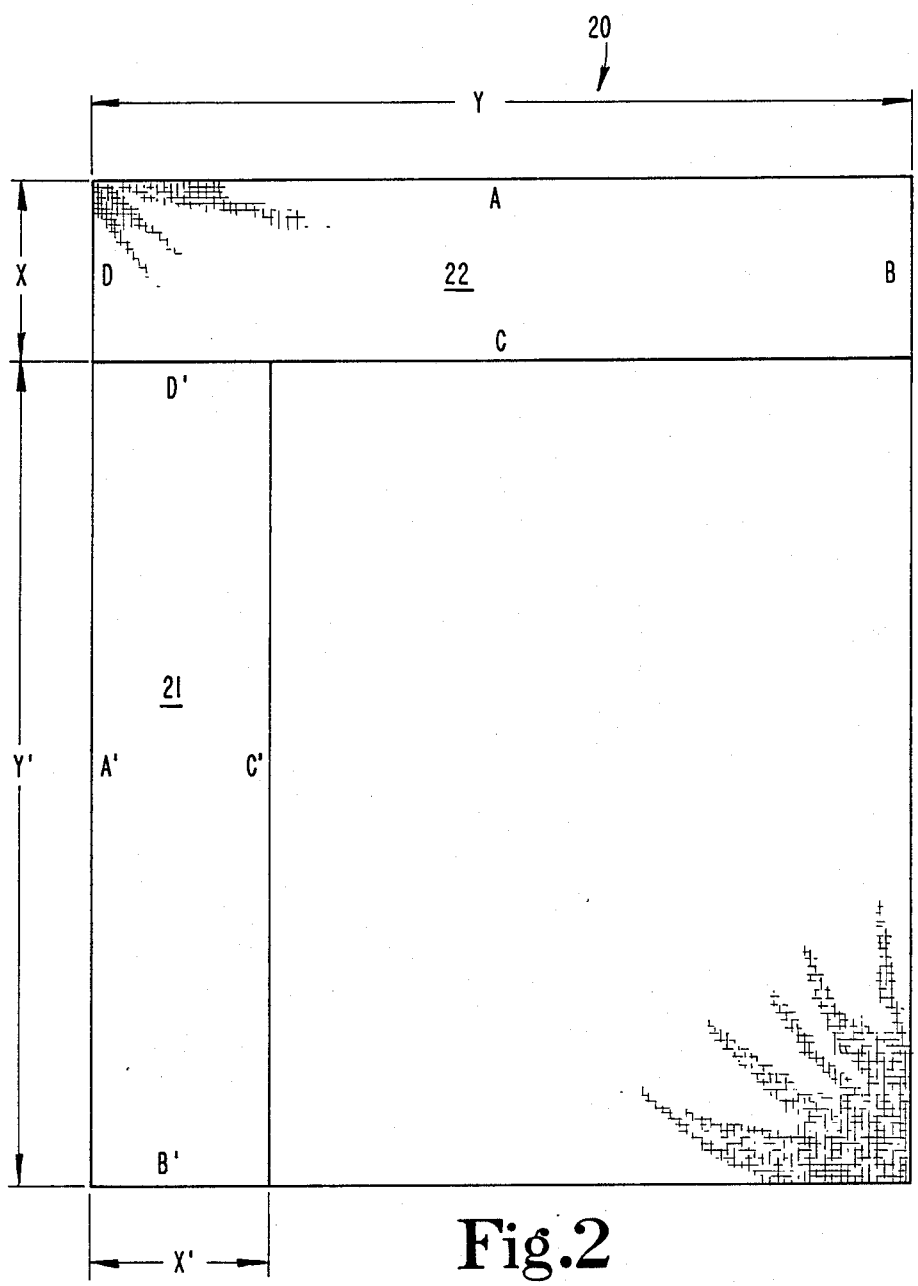
FIG. 2 is a schematic drawing of a sheet of material from which an examination garment may be constructed.

Referring now to FIG. 2, applicant's preferred method of constructing its preferred garment from the aforementioned SENSUA SOLIDS material shall be more particularly described. Shown is a schematic drawing of a sheet of the Sensua Solids material 20 with its dull side facing out from the page, and with its direction of dominant elasticity running vertically. This sheet 20 is divided into a generally rectangular section 21, which will be the inner ply of the final garment, and an equally sized generally rectangular section 22, which will be the outer ply of the final garment. By varying the lengths y and y' and the widths x and x' of sheets 21 and 22, garments of different sizes may be constructed to suit particular examinees. To date, applicant has preferably used the dimensions of 43" for y and y' and 9½" for x and x' to construct her garments.

Figure 3:
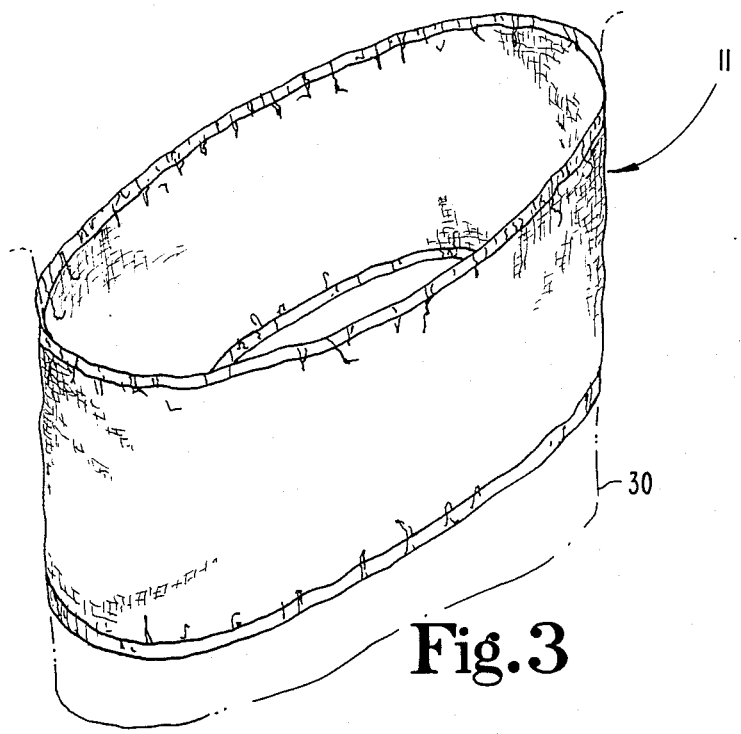
FIG. 3 is a perspective view of an examination garment which generally forms a continuous band of material and which can be worn completely around the torso of an examinee.

With continuing reference to FIG. 2, to construct applicant's preferred garment, sheets 21 and 22 are cut from sheet 20, and the dull side of sheet 21 is placed upon the dull side of sheet 22 so that A', B', C', and D' of sheet 21 align with the corresponding A, B, C, and D of sheet 22. Sides A and A' are thereafter joined together in a suitable manner such as stitching, and the same is done to side C and C', thus making a tube-like structure having sides AA', BB', CC', and DD'. Thereafter, this tube structure is turned inside out to configure the material so that the glossy surfaces of sheets 21 and 22 form the tube structure's inner surfaces. Sides AA' and CC' are thereafter elasticized, whereafter side BB' and side DD' are joined together by stitching or another suitable method, thus completing applicant's preferred examination garment 11 as shown in FIG. 3, which is a generally tube-shaped continuous band which can be worn completely around the torso 30.

To use applicant's preferred garment, the garment is placed around the upper torso of the examinee and worn over the breasts in the fashion of a "tube top". The innermost ply of the garment fits around the torso, and may also be form-fitted if desired. It extends up to and can be moved into the axillary area as desired. When the examiner's hand is thereafter run over portions of the garment covering areas to be examined for lumps or irregularities, the outer ply can freely slide on the skin touching ply so very little friction is encountered, and an effective physical examination for lumps and irregularities is conducted. Also, the outer ply of the garment may be made slightly larger than the inner ply so that, when their outer edges are stiched together, the outer ply fits loosely over the inner ply, thus facilitating a greater range of sliding motion in the examination process. This would also enable the inner ply to be sized to be snug-fitting on the examinee's body without the outer ply also being snug and interfering with the free sliding movement of the outer ply on the inner ply.

This garment has an additional advantage in that, if the person wears the garment while being examined, and the doctor notes an area that the patient should check periodically, the garment can be marked where the patient is to perform the specific periodic self-examinations at home.

Applicant contemplates that suitable garments incorporating the instant invention may be specially adapted for use with other parts of the body. Applicant also contemplates that the garments of her invention may be constructed of a suitable disposable material. Additionally, applicant recognizes that the features embodied in her invention are suitable for general application in areas where detection of irregularities or lumps in surfaces is desired.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A touch sensitive cancer detection garment to be worn during a tactile examination of the human body for lumps, in which the garment is worn over the area being examined, said garment comprising:
    (a) first and second plies having contacting surfaces which glide easily over each other due to a low coefficient of friction so that an effective tactile examination may be conducted of an area of the body over which the garment is worn; and
    (b) said first ply is located next to the skin when the garment is worn on the body and said second ply is sized slightly larger than said first ply such that when said second ply is secured to said first ply, said second ply fits loosely over said first ply to facilitate a greater range of sliding movement of said second ply relative to said first ply; and,
    (c) means for securing said plies together to form said garment; and,
    (d) said first ply is dominantly elastic in a first direction and said second ply is dominantly elastic in a second direction wherein, when said plies are joined together to form said garment, said first and second directions are substantially perpendicular to each other; and,
    (e) means for securing the garment on an area of the human body.

2. The garment of claim wherein said contacting surfaces exhibit a kinetic coefficient of friction of about 0.0–0.4.

3. The garment of claim 1 wherein said garment forms a generally tube-shaped continuous band which can be worn completely around the torso.

4. The garment of claim 1 wherein said first and second plies comprise about 85% nylon and about 15% spandex.

5. The garment of claim 1, wherein:
(a) said garment securing means comprises means for securing said plies to the breast area of the body with substantially consistent orientation upon repeated wearings.

6. The garment of claim 5, wherein:
(a) said securing means comprises bands of elastic material attached to said garment for holding said garment in place on a human body.

* * * * *